United States Patent
Beelen et al.

(10) Patent No.: US 10,821,277 B2
(45) Date of Patent: *Nov. 3, 2020

(54) KIT FOR AND METHOD OF ASSEMBLING AN APPLICATOR FOR INSERTING AN IMPLANT

(71) Applicant: MERCK SHARP & DOHME B.V., Haarlem (NL)

(72) Inventors: Dennis Cornelis Franciscus Beelen, Oss (NL); Martin Van Hermelen, Oss (NL); Robertus Theodoor Maria Moormann, Oss (NL); Maurice Petrus Wilhelmus Tak, Hengelo (NL)

(73) Assignee: MERCK SHARP & DOHME B.V., Haarlem (NL)

( * ) Notice: Subject to any disclaimer, the term of this patent is extended or adjusted under 35 U.S.C. 154(b) by 135 days.

This patent is subject to a terminal disclaimer.

(21) Appl. No.: 16/122,958

(22) Filed: Sep. 6, 2018

(65) Prior Publication Data

US 2019/0001111 A1   Jan. 3, 2019

Related U.S. Application Data

(63) Continuation of application No. 12/174,644, filed on Jul. 17, 2008, now Pat. No. 10,092,739, which is a (Continued)

(30) Foreign Application Priority Data

Jan. 19, 2006 (EP) .................................... 06100620

(51) Int. Cl.
*A61M 37/00* (2006.01)
*A61M 31/00* (2006.01)
*A61M 5/32* (2006.01)

(52) U.S. Cl.
CPC ...... *A61M 37/0069* (2013.01); *A61M 5/3202* (2013.01); *A61M 5/3204* (2013.01); (Continued)

(58) Field of Classification Search
CPC .............. A61M 37/0069; A61M 31/00; A61M 5/3202; A61M 5/3271; A61M 5/3204
(Continued)

(56) References Cited

U.S. PATENT DOCUMENTS 1,655,158 A   1/1928   Muir
2,269,963 A   1/1942   Wappler
(Continued)

FOREIGN PATENT DOCUMENTS

EP   0304107   2/1989
EP   596161    5/1994
(Continued)

*Primary Examiner* — Laura A Bouchelle
*Assistant Examiner* — Anh Bui
(74) *Attorney, Agent, or Firm* — Hoyng Rokh Monegier LLP; David P. Owen

(57) ABSTRACT

The invention pertains to a kit for assembling a disposable applicator for inserting an implant, in particular a rod-like implant containing an active substance, under the skin of a human or animal, the kit comprising a first component, in turn comprising a main housing part providing a handle for grasping and maneuvering the applicator, a cannula, and a cannula holder mounted in the main housing part, the main housing part having an opening which allows introduction of an implant into the proximal end of the cannula or the cannula holder, and, a second component for closing said opening, in turn comprising a second housing part and a rod attached to or forming an integral whole with the second housing part and mountable inside the cannula or the cannula holder.

10 Claims, 3 Drawing Sheets

Related U.S. Application Data continuation of application No. PCT/EP2007/050406, filed on Jan. 16, 2007.

(52) U.S. Cl.
CPC .......... *A61M 5/3271* (2013.01); *A61M 31/00* (2013.01); *A61M 37/00* (2013.01); *Y10T 29/49826* (2015.01)

(58) Field of Classification Search
USPC .............................. 604/57, 59–64, 192, 198
See application file for complete search history.

(56) References Cited

U.S. PATENT DOCUMENTS

| | | | |
|---|---|---|---|
| 2,643,653 | A | 6/1953 | Heidrich |
| 3,016,895 | A | 1/1962 | Sein |
| 3,538,916 | A | 11/1970 | Groff |
| 3,669,104 | A | 6/1972 | Wyatt |
| 3,766,915 | A | 10/1973 | Rychlik |
| 4,105,030 | A | 8/1978 | Kercso |
| 4,223,674 | A | 9/1980 | Fluent |
| 4,223,874 | A | 11/1980 | Fluent et al. |
| 4,451,253 | A | 5/1984 | Harman |
| 4,474,572 | A | 10/1984 | McNaughton |
| 4,597,753 | A | 7/1986 | Turley |
| 4,820,267 | A | 4/1989 | Harman |
| 4,834,708 | A | 5/1989 | Pillari |
| 4,994,028 | A | 2/1991 | Leonard et al. |
| 5,053,014 | A | 10/1991 | Van Heugten |
| 5,090,962 | A * | 2/1992 | Landry, Jr. .......... A61M 5/31511 604/110 |
| 5,135,493 | A | 8/1992 | Peschke |
| 5,147,295 | A * | 9/1992 | Stewart ............. A61M 37/0069 604/61 |
| 5,192,273 | A | 3/1993 | Bierman |
| 5,250,026 | A | 10/1993 | Ehrlich et al. |
| 5,279,554 | A | 1/1994 | Turley et al. |
| 5,348,544 | A | 9/1994 | Sweeney et al. |
| 5,395,319 | A | 3/1995 | Hirsch et al. |
| 5,484,403 | A | 1/1996 | Yoakum et al. |
| 5,695,463 | A | 12/1997 | Cherif-Cheikh et al. |
| 5,800,399 | A * | 9/1998 | Bogert ............. A61M 25/0014 604/164.11 |
| 5,827,297 | A | 10/1998 | Boudjema |
| 5,906,599 | A | 5/1999 | Kaldany et al. |
| 5,984,890 | A | 11/1999 | Gast et al. |
| 5,997,485 | A | 12/1999 | Ahmadzadeh |
| 6,007,474 | A | 12/1999 | Rydell |
| 6,102,844 | A | 8/2000 | Ravins et al. |
| 6,190,350 | B1 * | 2/2001 | Davis ................ A61M 37/0069 604/61 |
| 6,402,716 | B1 | 6/2002 | Ryoo et al. |
| 6,428,517 | B1 | 8/2002 | Hochman et al. |
| 6,478,768 | B1 | 11/2002 | Kneer |
| 6,544,239 | B2 | 4/2003 | Kinsey et al. |
| 6,589,157 | B2 | 7/2003 | Fontayne et al. |
| 6,592,508 | B1 | 7/2003 | Ravins et al. |
| 6,607,529 | B1 | 8/2003 | Jones et al. |
| D492,995 | S | 7/2004 | Rue et al. |
| 7,008,439 | B1 | 3/2006 | Janzen et al. |
| 7,214,206 | B2 | 5/2007 | Rue et al. |
| D551,759 | S | 9/2007 | Tak et al. |
| 7,604,647 | B2 | 10/2009 | Chen |
| 7,632,251 | B2 | 12/2009 | Lin et al. |
| 7,632,256 | B2 | 12/2009 | Mosler et al. |
| 7,766,924 | B1 | 8/2010 | Bombard |
| 7,963,972 | B2 | 6/2011 | Foerster et al. |
| 8,888,745 | B2 | 11/2014 | Van Der Graaf |
| 9,757,552 | B2 | 9/2017 | Jansen et al. |
| 2001/0031940 | A1 | 10/2001 | Loos |
| 2002/0026090 | A1 | 2/2002 | Kaplan et al. |
| 2002/0077599 | A1 | 6/2002 | Wojcik |
| 2003/0007992 | A1 | 1/2003 | Gibson et al. |
| 2003/0040699 | A1 | 2/2003 | Talling et al. |
| 2003/0220617 | A1 | 11/2003 | Dickerson |
| 2004/0199140 | A1 | 10/2004 | Rue et al. |
| 2004/0215133 | A1 | 10/2004 | Weber et al. |
| 2005/0261633 | A1 | 11/2005 | Khalaj |
| 2006/0058569 | A1 | 3/2006 | Chu |
| 2008/0221510 | A1 * | 9/2008 | Van Der Graaf .......................... A61M 37/0069 604/60 |
| 2009/0012463 | A1 | 1/2009 | Beelen et al. |
| 2009/0304992 | A1 | 12/2009 | Desimone et al. |
| 2010/0298807 | A1 | 11/2010 | Jansen et al. |

FOREIGN PATENT DOCUMENTS

| | | |
|---|---|---|
| EP | 0631794 | 1/1995 |
| EP | 0168168 | 9/2001 |
| EP | 1300129 A2 | 4/2003 |
| EP | 1300173 | 4/2003 |
| EP | 1323450 | 7/2003 |
| WO | 98/13092 | 4/1998 |
| WO | 9813091 | 4/1998 |
| WO | 9813092 | 4/1998 |
| WO | 98/58698 | 12/1998 |
| WO | 01/28631 | 4/2001 |
| WO | 01/68168 | 9/2001 |
| WO | 0168168 | 9/2001 |
| WO | 2004/089458 | 10/2004 |
| WO | 2006/077242 | 7/2006 |

* cited by examiner

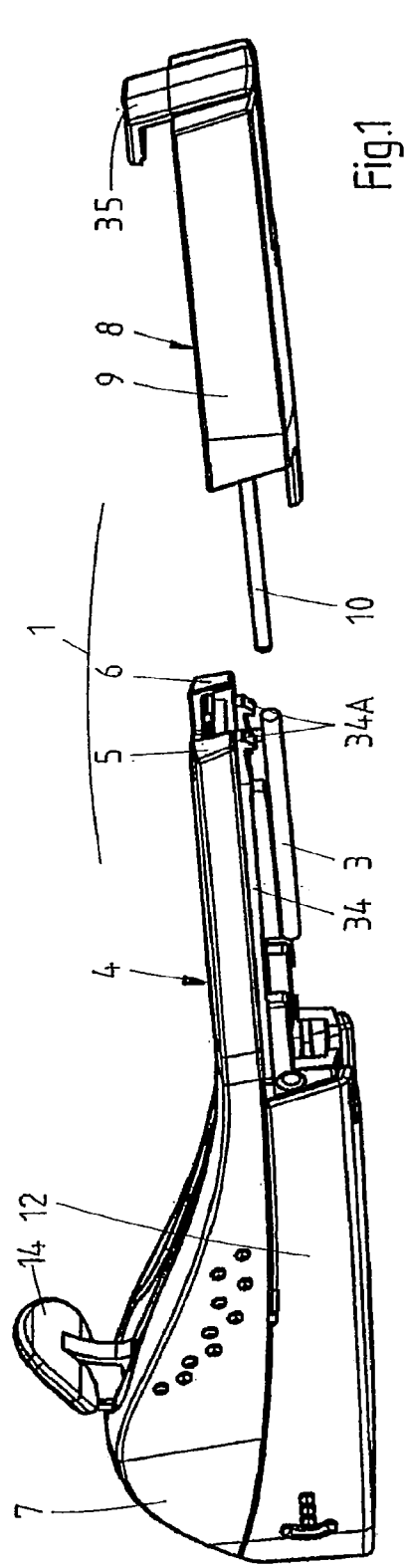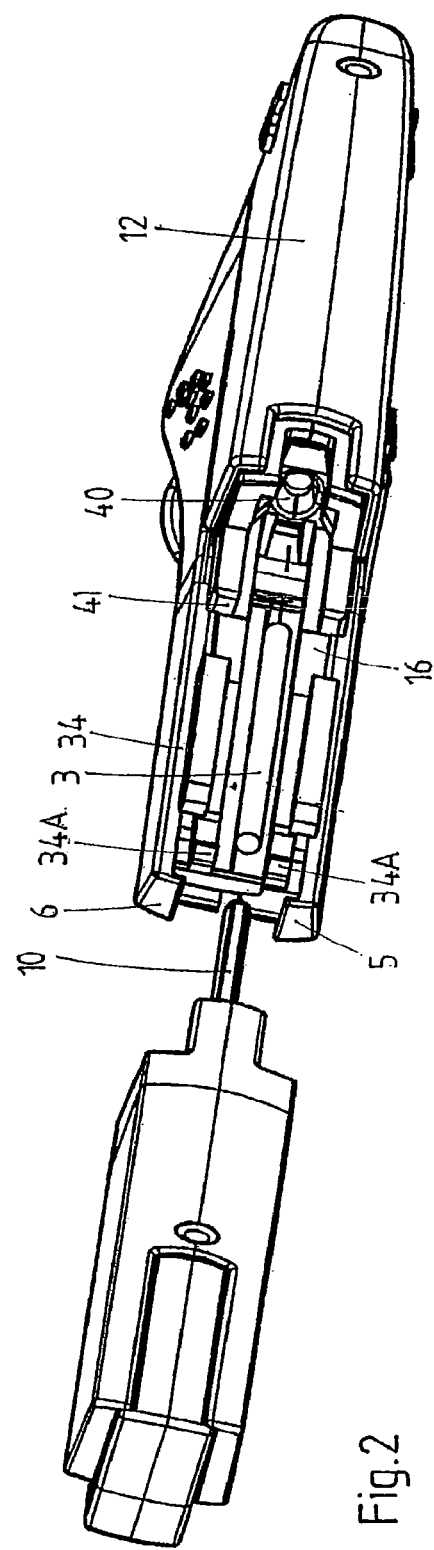

KIT FOR AND METHOD OF ASSEMBLING AN APPLICATOR FOR INSERTING AN IMPLANT

CROSS REFERENCE TO RELATED APPLICATIONS

This application is a continuation of U.S. application Ser. No. 12/174,644, filed on Jul. 17, 2008, which is a 371 of PCT application number PCT/EP2007/050406 filed on Jan. 16, 2007, which claims priority from EP application number 06100620.1 filed on Jan. 19, 2006. All applications are hereby incorporated by reference in their entireties.

BACKGROUND OF THE INVENTION

1. Field of the Invention

The invention relates to a kit for assembling a disposable applicator for inserting an implant, in particular a rod-like implant containing an active substance, under the skin of a human or animal. The invention further relates to a method of assembling an applicator.

2. Description of the Related Art

U.S. Pat. No. 4,820,267 relates to a device for subcutaneous implantation of single and plural elongated medicament pellets comprising a single dosage where magazine feeding is not applicable because considerations of sterility and cross-contamination require a fresh needle and obturator for each patient. The device includes a cannula supported at a proximal end thereof by a hub which slides within a tubular barrel, the barrel supporting an obturator which selectively penetrates the cannula to maintain an implanted pellet in position as the cannula is withdrawn. For single pellet dosages, the pellet is carried in the fore part of the cannula, while in the case of multiple pellet dosages, the additional pellets, prior to loading, are carried in open-ended cylindrical tubes engageable with a proximal end of the hub whereby the obturator may be employed to transfer the pellet to the cannula from the sleeve which is discarded. Repositioning of the hub within the sleeve is then accomplished without disengagement of the distal end of the cannula from the tissues of the patient and additional implantations may then be performed.

U.S. Pat. No. 3,016,895 relates to injectors, and more particularly to a veterinarian's injector of the type designed for subcutaneous implantation of solids in animals. U.S. Pat. No. 3,016,895 discloses a device wherein a longitudinally bored pellet receiving and loading unit is hingedly mounted so that it may be misaligned with the body of the injector, so that a solid pellet may be easily inserted therein, for convenient loading of the injector.

WO 2004/089458 relates to a device for inserting implantable objects beneath the skin of a patient, including a handle for grasping the device and a base connected to the handle. The base comprises a post, a cannula, and a flexible actuator positioned in an angled track. The cannula is positioned coaxially around and is longitudinally slidable over the post from an extended position, where an implantable object is retained in the cannula, to a retracted position, where the implantable object is released from the cannula. In operation the implanting device may be loaded with an implantable object either manually or with a cartridge. One embodiment of the device according to WO 2004/089458 is a kit which may include additional parts along with an implanting device which may be combined together to implant therapeutics, pharmaceuticals, or microencapsulated sensors into a patient. The kit may include the implanter in a first compartment. A second compartment may include a syringe, needles, scalpel, and any other instruments needed. A third compartment may include gloves, drapes, wound dressings and other procedural supplies for maintaining sterility of the implanting process, as well as an instruction booklet. A fourth compartment may include additional cannula and posts.

WO 01/68168 relates to a disposable device for inserting one or several implants, said device comprising a tubular cannula (10) provided with a tip (11), said cannula also serving as a container for the implants, a plunger (20) and a handle (30) having a first end (31) directed towards the cannula (10), and a second end (32) directed away from the cannula. The plunger (20) and the handle (30) are attached or attachable to each other in a fixed manner, and the cannula (10) is arranged to be movable in the longitudinal direction, so that the plunger (20) is placed therein. The device in WO 01/68168 is characterized in that i) the cannula (10) can, after inserting the implant or implants, be drawn on top of the plunger (20) so far, that the tip (11) of the cannula (10) becomes covered by the handle (30) or by a piece connected to the handle (30), and/or that ii) the cannula (10) is, when drawn to its extreme position, towards the second end (32) of the handle (30), arranged to be irretrievably locked in relation to the plunger (20).

EP 1 300 173 relates to a hand held implanter for containing and depositing a subcutaneous implant beneath the skin of a patient. FIGS. 11 to 13 illustrate one preferred method for loading the implant (18) into the implanter (110) in the case where the implanter is not preloaded by employing an implant containing vial (90). The vial (90) maintains the implant in a sterile condition during transportation, storage, and loading.

US 2001/0031940 relates to a device for administering implants. The device is a syringe-like device having a plunger, an injection cannula, and an active substance container there-between. The active substance container includes two retaining elements for preventing inadvertent dispensing of an implant. The retaining elements are flexible, and may be O-rings.

WO 98/58698 discloses an implantation device (1) comprising a hollow needle (2), preferably of the type having a chamfered tip profile, and a body (3) adjoining the needle part comprising a plunger (5), preferably having a chamfered tip profile capable of blending with the needle tip profile. The device is made preloadable by being provided with a chamber (7) capable of holding an implant (8), which chamber is positioned radially outside the periphery of the plunger (5) and has a directly or indirectly open connection to a channel (6) surrounding the plunger. The plunger is capable of closing off and opening up the chamber by being displaced.

In light of the above prior art, there is a particular need for a kit which can serve to reduce the risk of damaging the, often delicate, implant during (automated) introduction of the implant into a cannula and/or a cannula holder and which facilitates such introduction at a late stage of assembly of the applicator. This is particularly important in cases where the applicator comprises intricate design features to enhance e.g. ergonomics and/or operation safety.

BRIEF SUMMARY OF THE INVENTION

To this end, the kit according to the present invention comprises a first component, in turn comprising a main housing part providing a handle for grasping and maneuvering the applicator, a cannula, preferably extending from the housing, and a cannula holder mounted, preferably slidably, in the main housing part, the main housing part having an opening which allows introduction of an implant into the proximal end of the cannula and/or the cannula holder, and a second component for closing said opening, in turn comprising a second housing part at least partially complementary in shape to the main housing part and a rod attached to or forming an integral whole with the second housing part and mountable inside the cannula and/or the cannula holder.

Thus, the implant can be introduced into the proximal end of the cannula and/or the cannula holder avoiding contact with the tip of the cannula and such introduction can be postponed until just before the applicator is completed.

It is preferred that the first and second components are provided with complementary features for irreversibly attaching, e.g. snap fitting, one part to the other.

To facilitate proper alignment between the cannula and the implant during introduction, even if the implant is slightly curved due to storage on a reel, it is preferred that the distance between the opening in the main housing part, in particular the edge of the opening, and the proximal end of the lumen of the cannula and/or the cannula holder is less than the length of the implant to be used, preferably less than 20 mm, more preferably less than 10 mm or even less than 5 mm.

In a further embodiment the handle extends above at least 30%, preferably at least 50%, more preferably at least 80% or all of the length of the cannula extending from the first component.

The invention further pertains to a method of assembling a disposable applicator comprising the steps of sequentially: providing a first component comprising a main housing part; providing a handle for grasping and maneuvering the applicator, a cannula, preferably extending from the housing, and a cannula holder mounted, preferably slidably, in the main housing part, the main housing part having an opening which allows introduction of an implant into the proximal end of the cannula and/or the cannula holder, and, separate from the first component, a second component for closing the opening in the main housing part, in turn comprising a second housing part at least partially complementary in shape to the main housing part and a rod attached to or forming an integral whole with the second housing part; introducing an implant through the opening and into the proximal end of the cannula and/or the cannula holder; mounting the rod inside the cannula and/or the cannula holder and closing the opening by attaching, preferably irreversibly, one housing part to the other.

Finally, the invention relates to a disposable applicator obtained with this method, which applicator is contained inside a sterile package.

BRIEF DESCRIPTION OF THE DRAWINGS

The invention will now be explained in more detail with reference to the drawings, which schematically show a preferred embodiment according to the present invention.

FIGS. 1 and 2 are perspective views of a kit in accordance with the present invention.

DESCRIPTION OF ILLUSTRATIVE EMBODIMENTS

Figure 3:
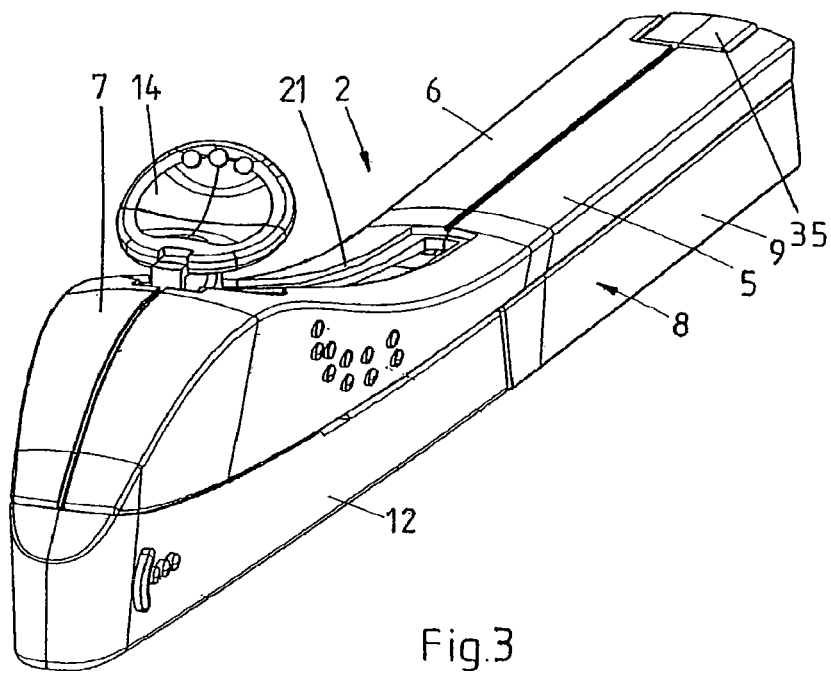
FIG. 3 is a perspective view of an applicator.

FIGS. 1 and 2 show a kit 1 in accordance with the present invention for assembling a disposable applicator 2 (shown in assembled condition in FIGS. 3 and 4) for inserting an implant 3, in particular a rod-like implant containing an active substance, such as a contraceptive, under the skin of a human. The applicator 2 may be of the type as described in co-pending U.S. application Ser. Nos. 11/795,796 and 11/795,805, the contents of both of which are hereby incorporated by reference in their entirety.

The kit 1 comprises a first component 4, in turn comprising a main housing part consisting of two half-shells 5, 6, welded together ultrasonically, and providing a handle 7 for grasping and maneuvering the applicator 2 (once assembled) and an open rear (proximal) section, and a second component 8, in turn comprising a second housing part consisting of a rear shell 9, complementary in shape to the main housing part 5, 6 and spanning at least 20% of the surface of the applicator 1 (once assembled), and a rod 10 attached to or forming an integral whole with the second housing part 9.

Figure 4:
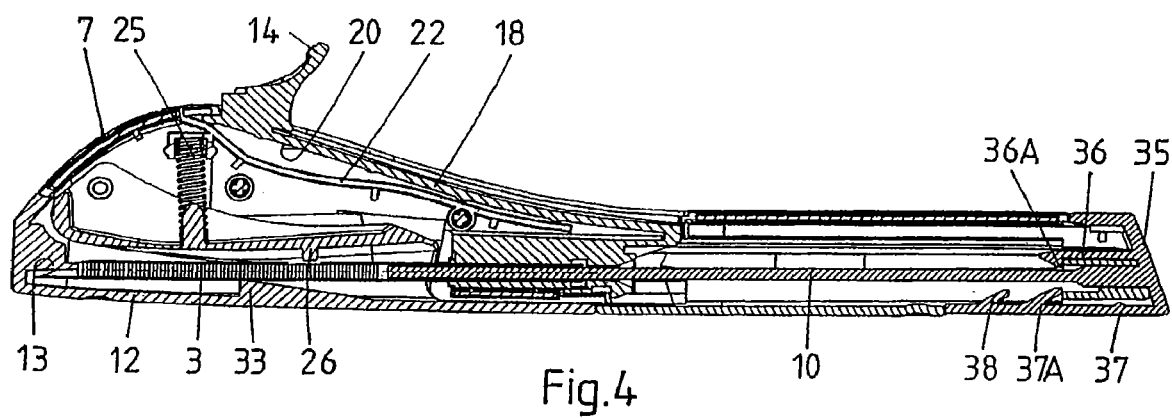
FIG. 4 is a cross-sectional side view of the applicator of FIG. 3.
Figure 5:
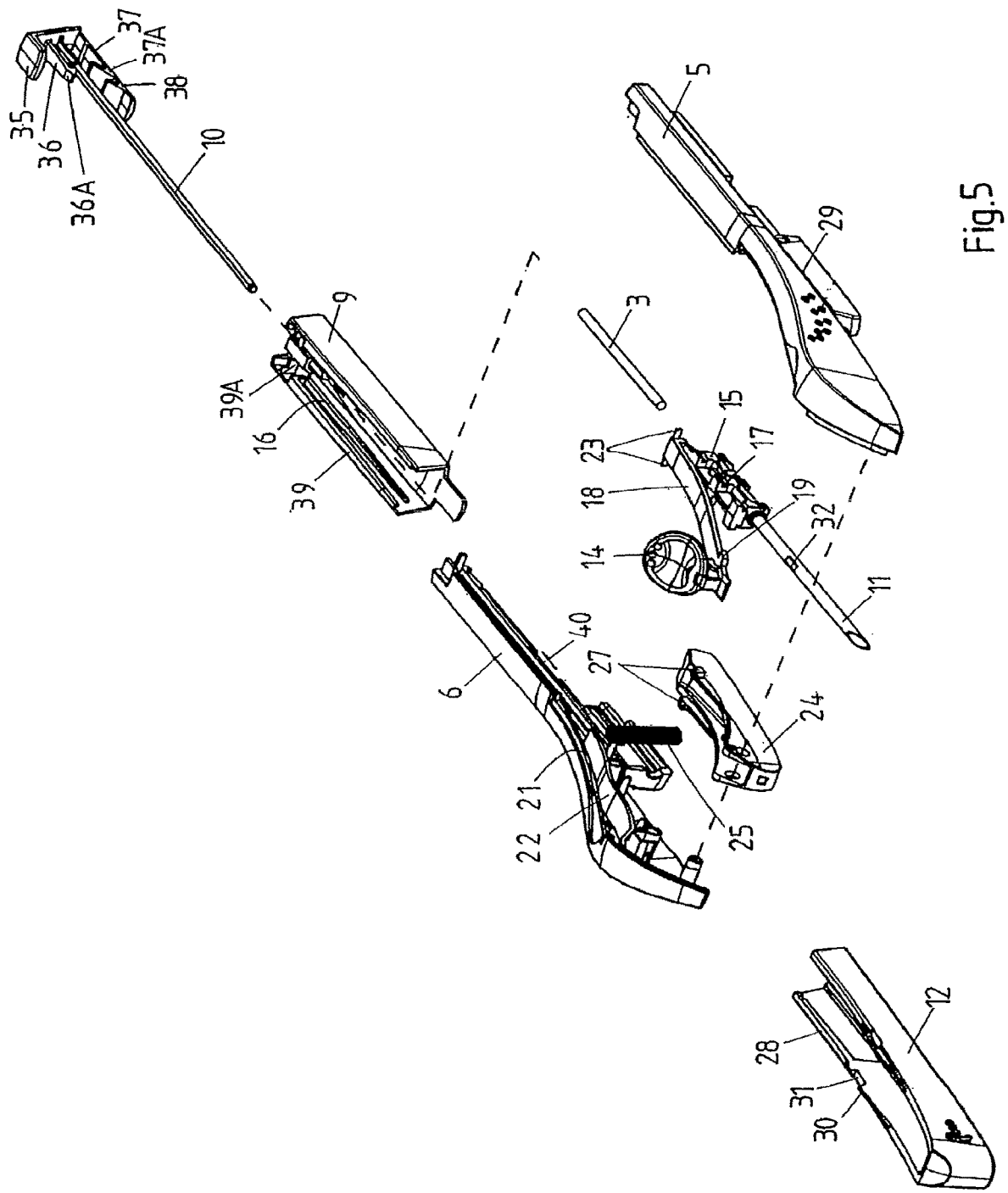
FIG. 5 is an exploded view of the applicator of FIG. 3.

With reference also to FIGS. 3 to 5, which show the assembled applicator (respectively an exploded view of the applicator), the first component 4 comprises a metal cannula 11 accommodating the implant 3, a protective cover 12 comprising a pin 13 extending into the tip of the cannula 11 to restrict the freedom of movement of the implant 3, and an actuator 14 for retracting the cannula 11 into the housing 5, 6, 9. The cannula 11 is fixed to a cannula holder 15 to form a cannula assembly, which is slidably received inside the housing 5, 6. To this end, the inner walls of the half-shells 5, 6 and the rear shell 9 are provided with parallel and longitudinal guides 16 and the cannula holder 15 is provided with corresponding longitudinal grooves 17 (FIG. 5). The cannula holder 15 is connected to the actuator 14 by means of a flexible element 18, which, in this example, forms an integral whole with the cannula holder 15 and the actuator 14. Depending on the configuration of the applicator, it may be more advantageous to employ a rigid element and/or a separate actuator, flexible element, and cannula holder, which are connected upon assembly of the applicator. The flexible element 18 comprises, on either side and preferably just below the actuator 14, lateral protrusions 19 (FIG. 5). The inner wall of the main housing part 5, 6 in turn comprises two corresponding stops 20 (FIG. 4), which prevent the protrusions 19 from passing and hence the actuator 14 from being pulled rearwards unintentionally. The lateral protrusions 19 and stops 20 also prevent the cannula holder 15 and the cannula 11 from being pushed rearwards during insertion.

On top of the handle 17, a track 21 is provided for guiding the actuator 14. A guide 22 is included just below the track 21, which is shaped to provide sufficient room below the actuator 14 to enable it to flex sufficiently far downwards to allow the lateral protrusions 19 to pass the stops 20, upon pushing the actuator 14 down. Retracting the cannula 11 thus can be performed in one flowing movement, i.e. upon applying pressure to the actuator 14, typically with an index finger, the actuator 14 flexes downwards, clearing the stops 20, and subsequently rearwards to the retracted position.

Also, two resilient lips 23 are provided on the rear (proximal) end of the cannula holder 15. The inner sidewalls of the main housing part 5, 6 in turn comprise two corresponding stops (not shown) that block rearward motion of the lips 23 and hence define the longitudinal position of the cannula holder 15 in rearward direction. It is preferred that this mechanism urges the cannula holder 15 into its most forward position, so as to prevent the implant 3 from extending from the cannula 11. Upon actuation, the lips 23 will flex inwards and past the stops.

A lever 24 is pivotally connected to the front end of the handle 7. The lever 24 is gently biased towards the cannula 11 by means of a spring 25 extending between the lever 24 and an inner wall of the handle 7. In the present example, the lever 24 interacts with the protective cover 12 and the implant 3. To this end, the lever 24 comprises a first protrusion 26 (FIG. 4) on its lower wall and a pair of lateral protrusions 27 (FIG. 5) on its upper rim.

The protective cover 12 (see in particular FIG. 5) on its inner walls comprises a pair of ridges 28 which, in combination with corresponding slots 29 on the outside of the half-shells 5, 6, impose sliding engagement between the cover 12 and the main housing part. The cover 12 further comprises, on its upper rim, a pair of keys 30, each interrupted by a notch 31.

The cannula 11 in turn comprises an opening 32 which allows the protrusion 26 to engage the implant 3 and thus to gently urge the implant 3 against the inner wall of the cannula 11.

With the protective cover 12 in place, the lateral protrusions 27 of the lever 24 are supported by the keys 30 and the first protrusion 26 is just clear of the implant 3.

If the protective cover 12 is removed, i.e. slid in longitudinal direction and away from the main housing part, the keys 30 will slide under the lateral protrusions 27. If no implant 3 is present inside the cannula 11, the protrusion 26 on the lever 24 is free to enter the cannula 11 through the opening 32 i.e. the lever 24 will drop when the lateral protrusions 27 reach the notches 31, thus blocking further movement of the cover 12, preventing the same from being removed and preventing the applicator from being used any further. If an implant 3 is present, the lever 24 will be lowered only very slightly, with the lateral protrusions 27 still clear of the notches 31, and yet causing the first protrusion 26 to rest, through the opening 32, on the implant 3, thus, on the one hand, allowing the cover 12 to be removed and, on the other, gently urging the implant 3 towards the inner wall of the cannula 11, i.e. securing the implant 3 inside the cannula 11.

The cover 12 further comprises, on its inner bottom wall, a stay 33 preferably having, in its top surface, a V-shaped groove extending in the longitudinal direction of the applicator 2. Upon placing the protective cover 12 onto the main housing part 5, 6, the stay 33 slightly lifts the cannula 11 and reproducibly defines the lateral position and height of the tip of the cannula 11 with respect to the pin 13, thus preventing contact between the tip of the cannula and the inner walls of the cover 12.

Finally, the main housing part 5, 6 comprises, preferably at the rear, at least one, e.g. two guides 34, and/or at least one, e.g. two resilient hooks 34A, for cooperation with corresponding features of the second housing part.

The second component 8 of the kit comprises a bracket 35, which has been inserted in and snap-fitted to the rear shell 9 by means of two resilient fingers 36, 37, each provided with a protrusion 36A, 37A. The lower finger 37 comprises, near its end, a second, preferably wedge-shaped, protrusion 38, which serves to lock the cannula holder 15 in its retracted position. The bracket 35 carries the aforementioned rod 10.

In this example, the length of the rod 10 is adjusted to the length of the lumen of the cannula holder 15 and the cannula 11 and the length of the implant 3, such that when the applicator is assembled and the cannula 11 is in the extended position, the implant 3 is fully contained inside the cannula 11 and typically abuts the distal end of the rod 10. When the cannula 11 is in the retracted position, the implant 3 is completely expelled from the cannula 11 and the distal end of the rod 10 extends from the distal end of the (retracted) cannula 11.

Finally, the rear shell 9 comprises at least one, e.g. two guides 39 for slidingly mounting the rear shell 9 onto the main housing part 5, 6 (in particular guides 34), and/or at least one feature, e.g. two ridges 39A, for snap-fitting the shell to the main housing 5, 6.

As will be clear from the explanations above, the main housing part comprises several sophisticated features that enhance ergonomics and/or safety of operation. Accordingly, it may occur, more frequently than in the case of more straightforward designs, that during production some applicators do not pass quality tests and are rejected. In such cases, the relatively expensive implant contained in the applicator is also lost.

With the kit according to the present invention, the implant can be introduced into the proximal end of the cannula and/or cannula holder after the first and second components have been approved and only just before the applicator is completed. Further, contact with the tip of the cannula during introduction of the implant can be avoided effectively.

To facilitate automated introduction of an implant, the proximal end of the lumen of the cannula 11 and/or cannula holder 15 is provided with a funnel-shaped entrance 40. To prevent the implant from contacting the upper rim of the cannula and hence to further reduce the risk of damaging the implant during insertion into the cannula, the diameter of the narrowest portion of the funnel-shaped entrance is equal to or smaller than the inner diameter of the cannula.

Also, the first component 4, in particular the main housing parts, can comprise features to enhance interaction with one or more tools. In this example, the main housing part 5, 6 comprises, in the edge of the open rear section, notches 41 to provide sufficient room for proper alignment of a tool for introducing the implant 3 into the cannula holder 15.

In this example, the kit 2 is produced by means of the following steps: introducing at least the proximal end of the cannula 11 in a mould and molding the cannula holder 15 about the proximal end, thus providing accurate alignment of entrance 40 of the cannula holder 15 and the cannula 11; positioning the cannula holder 15, the cannula 11, the actuator 14, the lever 24, and the spring 25 inside the half-shells 5, 6, and welding the same together ultrasonically; placing the cover 12 onto the main housing part 5, 6; attaching the rod 10 to the rear shell 9 and inspecting the thus obtained first and second components for compliance with production specifications.

The kit is now ready to receive an implant, either at the same facilities or elsewhere e.g. at the facilities where the implant is produced. The implant 3, which, in this example, is supplied in the form of a fiber wound on a large diameter reel, is introduced into the applicator 2 by means of the following steps: taking the end of the fiber from a reel and cutting the implant 3 to size; inspecting the implant 3; introducing the implant 3 through the open rear section of the first component 4 into the proximal end of the cannula 11 and/or the cannula holder 15; mounting the rod 10 inside the cannula 11 and/or the cannula holder 15 and closing the opening by snap fitting the second component 8 to the first component 4; and sterilizing and packaging the applicator 2.

The kit according to the present invention is especially suitable for use with delicate implants, in particular implants that slowly release an active substance over an extended period of time. A preferred example of such an implant is a single-rod contraceptive implant that provides protection against pregnancy for an extended period of time, e.g. 3 years. It consists of a non-biodegradable rod measuring 40 mm in length and 2 mm in diameter. After insertion, the rod slowly releases a progestogenic hormone, viz. etonogestrel.

The invention is not restricted to the above-described embodiments, which can be varied in a number of ways within the scope of the claims. For instance, in one embodiment at least the main and second housing parts, the cannula holder, and the rod are made of a synthetic material, for instance by means of injection molding. Accordingly, although specific embodiments have been described, these are examples only and are not limiting upon the scope of the invention.

What is claimed is:

1. A kit for assembling a disposable applicator for inserting an implant under the skin of a human or animal, the kit comprising: a first component comprising a main housing part, an actuator, a cannula, and a cannula holder, wherein the main housing part provides a handle for grasping and maneuvering the applicator, wherein the handle comprises a guiding means extending between the actuator and the main housing part, wherein the actuator is able to slide on the handle via the guiding means, wherein the cannula holder is slideably mounted in the main housing part and is fixed to the cannula and is designed to retract the cannula into the main housing part, wherein the main housing part has an opening at its proximal end which allows a user to insert the implant into a funnel-shaped entrance at a proximal end of the cannula holder located in the main housing part, the proximal end of the cannula holder being opposite to an insertion end of the cannula, and a second component separate from the first component for closing said opening, the second component comprising a second housing part and a rod, the second housing part at least partially complementary in shape to the main housing part and attachable thereto to form a single housing enclosing the cannula holder completely and so that the opening is thereby substantially completely closed, the rod being attached to or forming an integral whole with the second housing part, wherein the rod is mountable inside the cannula or the cannula holder, wherein the actuator is connected to the cannula holder so as to enable, once assembled, retracting the cannula and the cannula holder over the rod, wherein the implant is a non-biodegradable rod measuring 40 mm in length and 2 mm in diameter and containing etonogestrel.

2. The kit according to claim 1, wherein the first and second components are provided with complementary features for irreversibly attaching the main housing part to the second housing part.

3. The kit according to claim 1, wherein a distance between the opening and a proximal end of a lumen of the cannula or the cannula holder is less than 20 mm.

4. The kit according to claim 1, wherein a proximal end of a lumen of the cannula is provided with a funnel-shaped entrance.

5. The kit according to claim 4, wherein a diameter of a narrowest portion of the funnel-shaped entrance of the cannula or the cannula holder is equal to or smaller than an inner diameter of the cannula.

6. The kit according to claim 1, wherein the first component comprises a mechanism having a lever extending along at least part of the cannula, wherein the lever is rotatable or slidable or flexible between a first position, wherein the implant is secured inside the cannula or the cannula holder, and a second position, wherein the implant is disengaged.

7. The kit according to claim 1, wherein the second housing part is irreversibly mechanically attached to the main housing part.

8. The kit according to claim 1, wherein the assembled kit is enclosed within a sterile package.

9. The kit according to claim 1, wherein the opening in the main housing part for introduction of the implant is closed by attachment of the second component to the first component.

10. The kit according to claim 1, wherein the second component is configured so that the rod is mounted in the cannula or cannula holder by attachment of the second component to the first component.

* * * * *

UNITED STATES PATENT AND TRADEMARK OFFICE
CERTIFICATE OF CORRECTION

PATENT NO. : 10,821,277 B2
APPLICATION NO. : 16/122958
DATED : November 3, 2020
INVENTOR(S) : Dennis Beelen et al.

It is certified that error appears in the above-identified patent and that said Letters Patent is hereby corrected as shown below:

On the Title Page

Item (72), inventor 2 should read:
Martin van Harmelen

Signed and Sealed this
Ninth Day of February, 2021

Drew Hirshfeld
*Performing the Functions and Duties of the*
*Under Secretary of Commerce for Intellectual Property and*
*Director of the United States Patent and Trademark Office*